(12) United States Patent
Hill

(10) Patent No.: US 6,604,534 B2
(45) Date of Patent: Aug. 12, 2003

(54) PHYSICAL IMPROVEMENTS IN COATED MONOFILAMENT DENTAL TAPES

(75) Inventor: Ira D. Hill, Locust, NJ (US)

(73) Assignee: International Tape Partners, LLC, Stafford, TX (US)

( * ) Notice: Subject to any disclaimer, the term of this patent is extended or adjusted under 35 U.S.C. 154(b) by 0 days.

(21) Appl. No.: 09/935,922

(22) Filed: Aug. 23, 2001

(65) Prior Publication Data

US 2002/0083956 A1 Jul. 4, 2002

Related U.S. Application Data

(60) Provisional application No. 60/227,196, filed on Aug. 23, 2000, provisional application No. 60/227,239, filed on Aug. 23, 2000, provisional application No. 60/227,240, filed on Aug. 23, 2000, and provisional application No. 60/227,246, filed on Aug. 23, 2000.

(51) Int. Cl.⁷ ............................................... A67C 15/00
(52) U.S. Cl. ....................................................... 132/321
(58) Field of Search ................................. 132/321, 323, 132/329

(56) References Cited

U.S. PATENT DOCUMENTS

| | | | | |
|---|---|---|---|---|
| 3,153,418 A | 10/1964 | Fleming | | 132/93 |
| 3,800,812 A | 4/1974 | Jaffe | | 132/89 |
| 3,837,351 A | 9/1974 | Thornton | | 132/89 |
| 3,897,796 A | * 8/1975 | Erickson | | 132/321 |
| 3,942,539 A | 3/1976 | Corliss et al. | | 132/79 |
| 4,450,849 A | * 5/1984 | Cerceo et al. | | 132/321 |
| 4,776,358 A | 10/1988 | Lorch | | 132/321 |
| 4,911,927 A | 3/1990 | Hill et al. | | 424/443 |
| 4,974,615 A | 12/1990 | Doundoulakis | | 132/321 |
| 5,033,488 A | 7/1991 | Curtis et al. | | 132/321 |
| 5,057,310 A | 10/1991 | Hill et al. | | 424/52 |
| 5,098,711 A | 3/1992 | Hill et al. | | 424/401 |
| 5,165,913 A | 11/1992 | Hill et al. | | 424/49 |
| 5,209,251 A | 5/1993 | Curtis et al. | | 132/321 |
| 5,220,932 A | 6/1993 | Blass | | 132/321 |
| 5,433,226 A | 7/1995 | Burch | | 132/321 |
| 5,479,952 A | 1/1996 | Zachariades et al. | | 132/321 |
| 5,503,842 A | 4/1996 | Fazan et al. | | 260/621 |
| 5,518,012 A | 5/1996 | Dolan et al. | | 132/321 |
| 5,588,452 A | * 12/1996 | Peck | | 132/321 |
| RE35,439 E | 2/1997 | Rosenberger | | 132/321 |
| 5,609,170 A | * 3/1997 | Roth | | 132/321 |
| 5,711,935 A | 1/1998 | Hill et al. | | 424/49 |
| 5,718,251 A | 2/1998 | Gray et al. | | 132/321 |
| 5,755,243 A | 5/1998 | Roberts et al. | | 132/321 |
| 5,760,117 A | 6/1998 | Chen | | 524/270 |
| 5,765,576 A | 6/1998 | Dolan et al. | | 132/321 |
| 5,787,758 A | 8/1998 | Sheldon | | 74/490 |
| 5,845,652 A | 12/1998 | Tseng et al. | | 132/200 |
| 5,848,600 A | 12/1998 | Bacino et al. | | 132/321 |
| 5,865,197 A | * 2/1999 | Bible et al. | | 132/321 |
| 5,884,639 A | 3/1999 | Chen | | 132/321 |
| 5,911,228 A | 6/1999 | Curtis et al. | | 132/321 |
| 5,918,609 A | 7/1999 | Tsao et al. | | 132/321 |
| 5,962,572 A | 10/1999 | Chen | | 524/474 |
| 5,998,431 A | 12/1999 | Tseng et al. | | 514/300 |
| 6,003,525 A | 12/1999 | Katz | | 132/321 |
| 6,027,592 A | 2/2000 | Tseng et al. | | 156/167 |
| 6,083,208 A | 7/2000 | Modak et al. | | 604/265 |
| 6,148,830 A | 11/2000 | Chen | | 132/321 |
| 6,161,555 A | 12/2000 | Chen | | 132/321 |

* cited by examiner

Primary Examiner—Todd E. Manahan
(74) Attorney, Agent, or Firm—Ernest V. Linek; Banner & Witcoff, Ltd.

(57) ABSTRACT

Disclosed are coated monofilament dental tapes with physical improvements including patient-friendly edges and self-indicating releasable coatings.

7 Claims, 2 Drawing Sheets

PHYSICAL IMPROVEMENTS IN COATED MONOFILAMENT DENTAL TAPES

CROSS-REFERENCE TO RELATED APPLICATIONS

This application claims priority from the following copending U.S. Provisional Patent Applications—U.S.S. No. 60/227,196, U.S.S. No. 60/227,239, U.S.S. No. 60/227,240 and U.S.S. No. 60/227,246, each filed Aug. 23, 2000, the disclosures of which are hereby incorporated herein by reference.

BACKGROUND OF THE INVENTION

Monofilament interproximal devices are described and claimed in: U.S. Pat. Nos. Re 35,439; 3,800,812; 4,974,615; 5,760,117; 5,433,226; 5,479,952; 5,503,842; 5,755,243; 5,845,652; 5,884,639; 5,918,609; 5,962,572; 5,998,431; 6,003,525; 6,083,208; 6,148,830; 6,161,555; and 6,027,592, the disclosures of which are hereby incorporated herein by reference. These dental tapes generally have serious shortcomings in gentleness, in delivering coatings during flossing and in being handled easily and conveniently during flossing.

Polytetrafluoroethylene (PTFE) based interproximal devices are described in: U.S. Pat. Nos. 5,209,251; 5,033,488; 5,518,012; 5,911,228; 5,220,932; 4,776,358; 5,718,251; 5,848,600; 5,787,758; and 5,765,576. To date, no commercial versions of these tapes have been coated effectively and cannot be used to deliver active ingredients, interproximally and subgingivally during flossing. Handling during flossing is difficult. Most have to be folded to provide a consumer acceptable edge. Many are plagued with serious dimensional inconsistency problems, as well.

Monofilament dental tapes, in general, feature extraordinary shred resistance compared to multifilament dental flosses including those multifilament flosses described in the Hill, et al., U.S. Pat. Nos. 4,911,927; 5,057,310; 5,098,711; 5,165913; and 5,711,935.

The coated elastomeric monofilament tapes as described in Provisional Applications U.S.S. Nos. 60/227,433 and 60/227,255, respectively, offer the shred resistance of traditional monofilament tapes plus improved mouth feel, flavor impact, cleaning and hand. These attributes are responsible for the unexpected consumer preference of these coated elastomeric tapes over traditional monofilament tapes including PTFE tapes marketed under the trademark: Glide®, Easy Slide® and Total®.

SUMMARY OF THE INVENTION

The physical improvements in the monofilament tapes of the present invention include:

A "reduced-cutting-edge" effect which is achieved by extruding:
(a) rounded edges, or
(b) multiple rounded surfaces at an edge, or
(c) an edge so thin and flexible that it bends or folds on contact with soft tissue.

These various extruded edges cushion the impact of these modified monofilament tapes on soft tissue. The cushioning tape edges illustrated in FIGS. 1 to 4 of the drawings are achieved during extrusion of the monofilament tape prior to drawing, by using various shaped extrusion dies. These customized dies deliver the various changes to the monofilament tape cutting edge dimensions as shown in FIGS. 1 through 4.

As described above, the present invention is directed to physical improvements made to coated monofilament dental tape, particularly wherein said improvement is selected from the group consisting of:
(a) a reduced cutting edge wherein during monofilament tape extrusion, at least one lateral edge of said tape is formed into various shapes selected from the group consisting of: rounded shapes, multiple rounded shapes, thin flexible edges, multiple thin flexible edges and combinations thereof,
(b) feathered lateral tape edges comprising multiple fingers of varying densities and varying lengths introduced by various continuous cutting means applied to at least one edge of said tape after extrusion and prior to coating,
(c) self-indicating features incorporated into said coatings using a combination of colored tapes and colored tape coatings wherein various scribes applied to the coatings remove portions of the coating to form a visual predetermined design, and
(d) combinations thereof.

In certain preferred embodiments, the improved monofilament dental tape is improved in a manner such that the feathered lateral edge is selected from those illustrated in FIGS. 5 through 7 of the drawings.

In certain preferred embodiments, the improved monofilament dental tape is improved in a manner such that the self-indicating feature is selected from those illustrated in FIGS. 8 through 13 of the drawings.

Another preferred embodiment of the present invention is a process for physically improving coated monofilament dental tapes comprising carrying out at least one of the following steps:
(a) reducing the monofilament tape cutting edge effect, wherein during tape extrusion, at least one lateral edge of said tape is formed into various shapes selected from the group consisting of rounded shapes, multiple rounded shapes, thin flexible edges, multiple thin flexible edges and combinations thereof,
(b) forming feathered lateral tape edges after tape extrusion by applying continuous cutting means to at least one edge to produce lateral edge tape fingers at various densities and various lengths, and
(c) incorporating into colored monofilament tapes having colored coatings, various designs by removing a predetermined amount of said coating using scribe means to create a visual predetermined design in said coating.

Yet another preferred embodiment of the present invention comprises a method for improved cleaning of interproximal, subgingival and gingival margin areas of the oral cavity comprising flossing these areas with a coated monofilament dental tape having feathered lateral tape edges comprising multiple fingers of varying densities and varying lengths.

Yet another preferred embodiment of the present invention comprises a method for improved cleaning of interproximal, subgingival and gingival margin areas of the oral cavity comprising flossing these areas with a coated monofilament dental tape having at least one edge of said tape selected from the group consisting of rounded shapes, multiple rounded shapes, thin flexible edges, multiple thin flexible edges and combinations thereof.

DETAILED DESCRIPTION OF THE PREFERRED EMBODIMENTS

Figure 1:
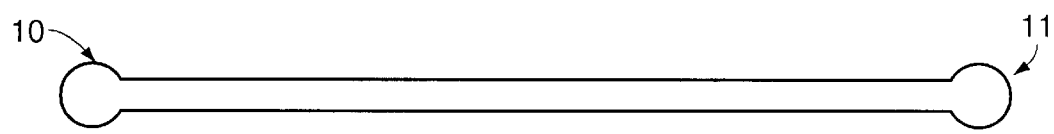
FIG. 1 illustrates monofilament tapes with "bulbous" edges, 10 and 11. These rounded edges are preferably longer in diameter than the thickness of the monofilament tape.
Figure 2:
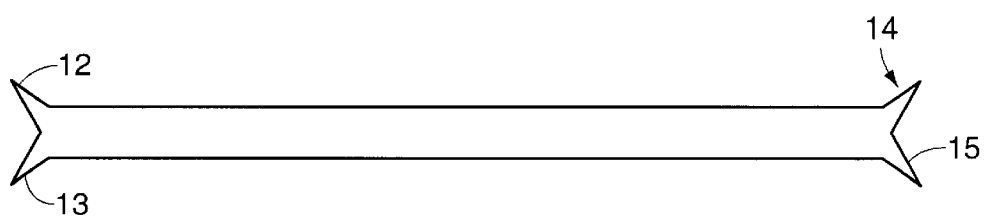
FIG. 2 illustrates monofilament tape with multiple feathered edges, 12–15, that have a tendency to "fold over" when brought into contact with soft tissue.
Figure 3:
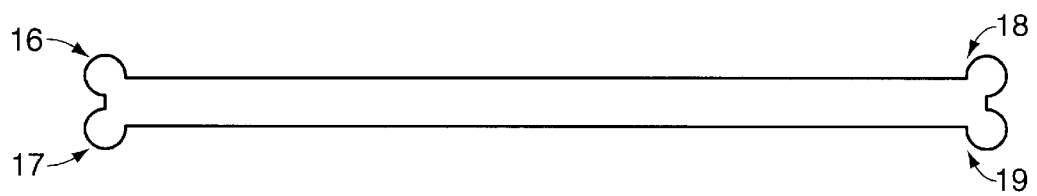
FIG. 3 illustrates monofilament tape with a barbell shape, where the rounded nodules, 16–19, contact soft tissue rather than the sharp edges characteristic of traditional monofilament tapes.
Figure 4:
FIG. 4 illustrates a thinned edge monofilament tape with the tendency of the thinned edges, 20 and 21, to fold over when brought into flossing contact with soft tissue.

Dental tapes of the prior art tapes are flat, i.e., they have parallel edges. Traditional dental tapes, and preferably the coated elastomeric monofilament tapes described in Tables 1–5 below, can be physically improved in accordance with this invention, thereby improving the following key consumer attributes, gentleness, physical cleaning and visual signals. See in particular, FIGS. 1 through 8 of the drawings.

TABLE 1

TAPE COMPOSITION

| Ex. No. | Thermoplastic Elastomer Type | Manufacturer | Trade name | Grade | Silicone Process Aid (%) | TiO$_2$ (%) | Secondary Polymer added Type (%) | Other Add'n Type (%) |
|---|---|---|---|---|---|---|---|---|
| 2 | PEBA polyester amide | Atofina | PEBAX | 55/33 | 3.5 | 1.8 | PP-4.7 | — |
| 3 | PEBA polyester amide | " | " | " | 3.5 | 1.8 | PP-4.7 Adflex-5 | — |
| 4 | PEBA polyester amide | " | " | " | 3.5 | 1.8 | PP-9.7 | — |
| 5 | PEBA polyester amide | Atofina | PEBAX | 63/33 | 0 | 0 | 0 | — |
| 6 | PEBA polyester amide | " | " | " | 0 | 1.8 | PP-1.2 | — |
| 7 | PEBA polyester amide | " | " | " | 3.5 | 1.8 | PP-4.7 | — |
| 8 | PEBA polyester amide | " | " | " | 3.5 | 1.8 | PP-4.7 Adflex-5 | — |
| 9 | PEBA polyester amide | " | " | " | 3.5 | 1.8 | PP-9.7 | — |
| 10 | PEBA polyester amide | " | " | " | 3.5 | 1.8 | PP-4.7 Nylon 11-5 | — |
| 11 | TPE polyether ester | DuPont | Hytrel | 6359FG | 2.3 | 1.0 | 0 | Ca Stearate 0.1 |
| 12 | TPE polyether ester | " | " | " | 3.5 | 1.8 | PP-4.7 | Ca Stearate 0.1 |
| 13 | TPE-E polyether ester | DSM | Arnitel | PM581 | 0 | 0 | 0 | — |
| 14 | TPE-E polyether ester | " | " | " | 0 | 1.8 | PP-1.2 | — |
| 15 | TPE-E polyether ester | " | " | " | 3 | 0 | PBT-5 | — |
| 16 | TPE-E polyether ester | " | " | " | 0 | 0 | PBT-5 | — |
| 17 | TPE-E polyether ester | " | " | " | 0 | 1.8 | PP-l.2 PBT-5 | — |

| | PROCESSING CONDITIONS | | | PROPERTIES | | | DIMENSIONS | | | UTILITY FACTORS | | | |
|---|---|---|---|---|---|---|---|---|---|---|---|---|---|
| Ex. No. | Melt Temp °C. | Draw Temp °C. | Draw Ratio | Break Strength in Newtons | Elongation to Break (%) | Elastic Limit (%) | Decitex | Width (mm) | Thick (mm) | Gentleness Perception | Tape Flex Twist Index | Hardness Shore D | |
| 2 | 260 | 130 | 6.8:1 | 30 | 26 | 0 | 750 | 1.30 | 0.063 | 6 | 4 | 37 | |
| 3 | 260 | 130 | 6.5:1 | 27 | 18 | 0 | 760 | 1.30 | 0.063 | 6 | 4 | 37 | |
| 4 | 260 | 130 | 6.8:1 | 26 | 19 | 0 | 760 | 1.30 | 0.063 | 6 | 4 | 37 | |
| 5 | 260 | 135 | 6:1 | 30 | 15 | 0 | 805 | 1.44 | 0.065 | 5.5 | 4 | 36 | |
| 6 | 260 | 135 | 6.3:1 | 32.36 | 13 | 0 | 800 | 1.41 | 0.067 | 5.5 | 4 | 36 | |
| 7 | 260 | 135 | 6.2:1 | 33.47 | 17 | 0 | 860 | 1.36 | 0.066 | 5.5 | 4 | 36 | |
| 8 | 260 | 135 | 6.2:1 | 25.94 | 14 | 0 | 810 | 1.32 | 0.078 | 5.5 | 4 | 36 | |
| 9 | 260 | 135 | 6.2:1 | 29.46 | 14 | 0 | 780 | 1.34 | 0.069 | 5.5 | 4 | 36 | |
| 10 | 260 | 135 | 6.2:1 | 30.63 | 13 | 0 | 810 | 1.30 | 0.065 | 5.5 | 4 | 36 | |
| 11 | 225 | 130 | 5:1 | 20 | 20 | 15 | 1400 | 1.70 | 0.070 | 7 | 3 | 33 | |
| 12 | 225 | 140 | 5.7:1 | 24 | 14 | 10 | 1230 | 1.70 | 0.070 | 7 | 3 | 33 | |
| 13 | 235 | 140 | 4.3:1 | 18 | 13 | 10 | 1500 | 1.63 | 0.084 | 7 | 3 | 33 | |

TABLE 1-continued

| | | | | | | | | | | | |
|---|---|---|---|---|---|---|---|---|---|---|---|
| 14 | 240 | 115 | 4.3:1 | 19 | 14 | 5 | 1634 | 1.64 | 0.085 | 7 | 3 | 33 |
| 15 | 235 | 140 | 4.3:1 | 19 | 10 | 3 | 1580 | 1.68 | 0.079 | 7 | 3 | 33 |
| 16 | 235 | 140 | 4.3:1 | 18 | 12 | 2 | 1500 | 1.70 | 0.086 | 7 | 3 | 33 |
| 17 | 235 | 140 | 4.3:1 | 21 | 15 | 4 | 1575 | 1.77 | 0.083 | 7 | 3 | 33 |

TABLE 2

TAPE COMPOSITION

| Ex. No. | Thermoplastic Elastomer Type | Manufacturer | Tradename | Grade | Silicone Process Aid (%) | TiO₂ (%) | Secondary Polymer added Type (%) | Other Add'n Type (%) |
|---|---|---|---|---|---|---|---|---|
| 18 | TPE-E polyether ester | DSM | Arnitel | EM550 | 0 | 0 | 0 | — |
| 19 | TPE-E polyether ester | " | " | " | 0 | 1.8 | PP-1.2 | — |
| 20 | TPE-E polyether ester | " | " | " | 0 | 1.8 | PP-6.2 | — |
| 21 | TPE-E polyether ester | " | " | " | 0 | 0 | PBT-5 | — |
| 22 | TPE-P polyether ester | OSM | Arnitel | EM630 | 0 | 0 | 0 | — |
| 23 | TPE-P polyether ester | " | " | " | 0 | 1.8 | PP-1.2 | — |
| 24 | TPE-P polyether ester | " | " | " | 0 | 1.8 | PP-1.2 Adflex-5 | — |
| 25 | TPE-P polyether ester | " | " | " | 0 | 1.8 | PP-6.2 | — |
| 26 | TPE-P polyether ester | " | " | " | 0 | 0 | PBT-5 | — |
| 27 | TPE-P polyester ester | DSM | Arnitel | UM552 | 0 | 0 | 0 | — |
| 28 | TPE-P polyester ester | " | " | " | 0 | 0 | 0 | Ca Stearate 0.1 |
| 29 | TPE-P polyester ester | " | " | " | 0 | 1.8 | PP-1.2 | — |
| 30 | TPE-P polyester ester | " | " | " | 0 | 0 | Adflex-5 | — |
| 31 | TPE-P polyester ester | " | " | " | 0 | 1.5 | PP-1.2 PBT-5 | Ca Stearate 0.1 |
| 32 | TPE-P polyester ester | " | " | " | 0 | 0 | PBT-5 | Ca Stearate 0.1 |
| 33 | EPDM TPV | Monteil | Adflex | Q100F | 0 | 0 | PP-20 | — |
| 34 | EPDM TPV | " | " | " | 3.5 | 1.8 | PP-24.7 | — |
| 35 | EPDM TPV | " | " | " | 7 | 3 | PP-30 | — |
| 36 | EPDM TPV | " | " | " | 7 | 3 | PP-34.7 | — |
| 37 | EPDM TPV | " | " | " | 7 | 3 | PP-40 | — |

| PROCESSING CONDITIONS | | | PROPERTIES | | DIMENSIONS | | | UTILITY FACTORS | | | |
|---|---|---|---|---|---|---|---|---|---|---|---|
| Ex. No. | Melt Temp °C. | Draw Temp °C. | Draw Ratio | Break Strength in Newtons | Elongation to Break (%) | Elastic Limit (%) | Decitex | Width (mm) | Thickness (mm) | Gentleness Perception | Tape Flex-Twist Index | Hardness Shore D |
| 18 | 240 | 140 | 4.3:1 | 23 | 25 | 7 | 1800 | 1.95 | 0.096 | 7 | 3 | 33 |
| 19 | 240 | 115 | 6:1 | 27 | 11 | 5 | 1050 | 1.47 | 0.071 | 7 | 3 | 33 |
| 20 | 240 | 140 | 5.6:1 | 26 | 17 | 5 | 1216 | 1.45 | 0.071 | 7 | 3 | 33 |
| 21 | 240 | 145 | 5.9:1 | 28 | 145 | 5 | 1220 | 1.55 | 0.074 | 7 | 3 | 33 |
| 22 | 235 | 150 | 4.5:1 | 18 | 12 | 4 | 1090 | 1.44 | 0.067 | 7 | 3 | 33 |
| 23 | 235 | 150 | 4.7:1 | 17 | 11 | 4 | 1130 | 1.50 | 0.068 | 7 | 3 | 33 |
| 24 | 235 | 150 | 4.6:1 | 18 | 10 | 7 | 961 | 1.35 | 0.065 | 7 | 3 | 33 |
| 25 | 235 | 150 | 4.6:1 | 14 | 30 | 10 | 965 | 1.24 | 0.073 | 7 | 3 | 33 |
| 26 | 235 | 150 | 4.6:1 | 20 | 12 | 5 | 1018 | 1.39 | 0.069 | 7 | 3 | 33 |
| 27 | 240 | 150 | 6.6:1 | 32 | 12 | 8 | 1300 | 1.49 | 0.070 | 7.5 | 3.5 | 31 |
| 28 | 230 | 150 | 5.6:1 | 26 | 15 | 8 | 1090 | 1.40 | 0.070 | 7.5 | 3.5 | 31 |
| 29 | 240 | 150 | 6.3:1 | 29 | 16 | 8 | 1150 | 1.46 | 0.070 | 7.5 | 3.5 | 31 |

TABLE 2-continued

| | | | | | | | | | | | |
|---|---|---|---|---|---|---|---|---|---|---|---|
| 30 | 230 | 140 | 5.6:1 | 30 | 16 | 10 | 1233 | 1.48 | 0.069 | 7.5 | 3.5 | 31 |
| 31 | 230 | 145 | 5.7:1 | 22 | 19 | 10 | 1108 | 1.53 | 0.067 | 7.5 | 3.5 | 31 |
| 32 | 230 | 245 | 5.3:1 | 24 | 14 | 8 | 1143 | 1.48 | 0.064 | 7.5 | 3.5 | 31 |
| 33 | 240 | 130 | 4.5:1 | 26 | 20 | 0 | 910 | 1.60 | 0.064 | 5.5 | NT | NT |
| 34 | 240 | 130 | 4.5:1 | 25 | 24 | 0 | 940 | 1.59 | 0.064 | 5.5 | NT | NT |
| 35 | 240 | 130 | 4.7:1 | 28 | 20 | 0 | 870 | 1.58 | 0.064 | 5.5 | NT | NT |
| 36 | 240 | 130 | 4.7:1 | 27 | 23 | 0 | 880 | 1.58 | 0.060 | 5.5 | NT | NT |
| 37 | 240 | 130 | 4.7:1 | 35 | 18 | 0 | 720 | 1.44 | 0.063 | 5 | NT | NT |

TABLE 3

TAPE COMPOSITION

| Ex. No. | Thermoplastic Elastomer Type | Manufacturer | Tradename | Grade | Silicone Process Aid (%) | $TiO_2$ (%) | Secondary Polymer added Type (%) | Other Add'n Type (%) |
|---|---|---|---|---|---|---|---|---|
| 38 | PEBA polyester amide | Atofina | PEBAX | 55133 | 0 | 1.8 | PP-1.2 | — |
| 39 | PEBA polyester amide | " | " | " | 3.5 | 1.8 | PP-4.7 EMA-3 | — |
| 40 | PEBA polyester amide | " | " | " | 3.5 | 1.8 | PP-4.7 | — |
| 41 | PEBA | Atofina | PEBAX | 63/33 | 3.5 | 1.8 | PP-4.7 EMA-3 | — |
| 42 | " | " | " | " | 0 | 0 | Nylon 11-5 | PDVF-3 |
| 43 | TPE-E polyether ester | DSM | Arnitel | PM581 | 3 | 0 | 0 | — |
| 44 | TPE-E polyether ester | DSM | Arnitel | EM550 | 3 | 0 | 0 | — |
| 45 | TPE-E polyether ester | " | " | " | 3 | 1.8 | PP-1.2 EMA-3 | — |
| 46 | TPE-E polyether ester | DSM | Arnitel | UM552 | 3 | 1.8 | PP-1.2 | — |

| | PROCESSING CONDITIONS | | PROPERTIES | | DIMENSIONS | | | UTILITY FACTORS | | | |
|---|---|---|---|---|---|---|---|---|---|---|---|
| Ex. No. | Melt Temp °C. | Draw Temp °C. | Draw Ratio | Break Strength in Newtons | Elongation to Break (%) | Elastic Limit (%) | Decitex | Width (mm) | Thickness (mm) | Gentleness Perception | Tape Flex-Twist Index | Hardness Shore D |
| 38 | 260 | 130 | 6.8:1 | 28 | 24 | 0 | 775 | 1.30 | 0.063 | 6 | 4 | 37 |
| 39 | 260 | 130 | 7:1 | 28 | 30 | 3 | 750 | 1.30 | 0.063 | 8 | 4 | 37 |
| 40 | 260 | 130 | 6.8:1 | 29 | 24 | 0 | 800 | 1.35 | 0.070 | 6 | 4 | 37 |
| 41 | 260 | 135 | 6.5:1 | 31 | 20 | 3 | 800 | 1.40 | 0.065 | 5.5 | 4 | 36 |
| 42 | 260 | 135 | 6.2:1 | 28 | 14 | 0 | 800 | 1.30 | 0.065 | 5.5 | 4 | 36 |
| 43 | 235 | 140 | 5:1 | 22 | 16 | 7 | 1400 | 1.60 | 0.079 | 7 | 3 | 33 |
| 44 | 240 | 140 | 6:1 | 25 | 20 | 7 | 800 | 1.30 | 0.060 | 7 | 3 | 33 |
| 45 | 240 | 140 | 6:1 | 27 | 15 | 5 | 850 | 1.35 | 0.065 | 7 | 3 | 33 |
| 46 | 240 | 150 | 6:1 | 27 | 17 | 10 | 1100 | 1.47 | 0.069 | 7.5 | 3 | 33 |

TABLE 4

TAPE COMPOSITION

| Ex. No. | Thermoplastic Elastomer Type | Manufacturer | Tradename | Grade | Silicone Process Aid (%) | $TiO_2$ (%) | Secondary Polymer added Type (%) | Other Add'n Type (%) |
|---|---|---|---|---|---|---|---|---|
| 47 | Styrenics SEBS | Alphagary | Evoprene | G978 | 0 | 1.8 | PP-1.2 | — |
| 48 | Styrenics SEBS | " | " | " | 3 | 1.8 | PP-1.2 | — |
| 49 | Styrenics SEBS | " | " | " | 0 | 1.8 | PP-1.2 EMA-3 | — |
| 50 | Styrenics SEBS | " | " | " | 3.5 | 1.8 | PP-9.7 | — |
| 51 | Styrenics SEBS | " | " | " | 3.5 | 1.8 | PP-9.7 PS-5 | — |

TABLE 4-continued

| Ex. No. | | | | | | | |
|---|---|---|---|---|---|---|---|
| 52 | TPU 90AEN | Dow | Pelethane | 2103- | 0 | 1.8 | PP-1.2 | — |
| 53 | TPU 90AEN | " | " | " | 3 | 1.8 | PP-1.2 | — |
| 54 | TPU 90AEN | " | " | " | 0 | 1.8 | PP-1.2 EMA-3 | — |
| 55 | TPU 90AEN | " | " | " | 3.5 | 1.8 | PP-9.7 | — |
| 56 | TPV | DSM | Sarlink | 4149D | 0 | 1.8 | PP-1.2 | — |
| 57 | " | " | " | " | 3 | 1.8 | PP-1.2 | — |
| 58 | " | " | " | " | 0 | 1.8 | PP-1.2 EMA-3 | — |
| 59 | " | " | " | " | 3 | 1.8 | PP-6.2 | |

| | PROCESSING CONDITIONS | | PROPERTIES | | DIMENSIONS | | | UTILITY FACTORS | | | |
|---|---|---|---|---|---|---|---|---|---|---|---|
| Ex. No. | Melt Temp °C. | Draw Temp °C. | Draw Ratio | Break Strength in Newtons | Elongation to Break (%) | Elastic Limit (%) | Decitex | Width (mm) | Thickness (mm) | Gentleness Perception | Tape Flex-Twist Index | Hardness Shore D |
| 47 | 200 | 100 | 7:1 | 19 | 30 | 10 | 1100 | 1.30 | 0.060 | 6 | 4 | 37 |
| 48 | 200 | 100 | 7:1 | 20 | 35 | 12 | 1100 | 1.30 | 0.060 | 6 | 4 | 37 |
| 49 | 200 | 100 | 7.2:1 | 17 | 32 | 12 | 1100 | 1.30 | 0.060 | 6 | 4 | 37 |
| 50 | 200 | 100 | 7:1 | 14 | 20 | 7 | 1100 | 1.30 | 0.060 | 8 | 4 | 37 |
| 51 | 200 | 100 | 7:1 | 22 | 28 | 8 | 1100 | 1.30 | 0.060 | 6 | 4 | 37 |
| 52 | 230 | 120 | 7:1 | 32 | 15 | 5 | 1200 | 1.40 | 0.068 | 7 | 3 | 33 |
| 53 | 230 | 120 | 6:1 | 30 | 17 | 6 | 1200 | 1.40 | 0.068 | 7 | 3 | 33 |
| 54 | 230 | 120 | 6:1 | 26 | 16 | 6 | 1200 | 1.40 | 0.068 | 7 | 3 | 33 |
| 55 | 230 | 120 | 5:1 | 22 | 10 | 2 | 1300 | 1.45 | 0.070 | 7 | 3 | 33 |
| 56 | 220 | 105 | 4.5:1 | 20 | 20 | 5 | 1400 | 1.45 | 0.072 | 6 | 4 | 37 |
| 57 | 220 | 105 | 5:1 | 22 | 35 | 7 | 1300 | 1.40 | 0.070 | 6 | 4 | 37 |
| 58 | 220 | 105 | 4.8:1 | 19 | 20 | 5 | 1350 | 1.48 | 0.075 | 6 | 4 | 37 |
| 59 | 220 | 105 | 4.2:1 | 15 | 20 | 5 | 1450 | 1.48 | 0.075 | 6 | 4 | 37 |

Saliva soluble coatings for monofilament tapes to be bobbin wound according to the present invention are described in Table 5. In the Table, the term "Ultramulsion 10-2.5" is defined as an emulsion of polydimethylsiloxane (PDMS) at 2.5 million cs in a nonionic surfactant Poloxamer 407, where the PDMS is at 10% by weight of the total emulsion.

TABLE 5

| EXAMPLE | 60 | 61 | 62 | 63 | 64 | 65 | 66 | 67 | 68 | 69 | 70 | 71 | 72 | 73 | 74 | 75 | 76 | 77 |
|---|---|---|---|---|---|---|---|---|---|---|---|---|---|---|---|---|---|---|
| Ingredient | | | | | | | | | | | | | | | | | | |
| Ultramulsion 10-2.5 | 57.1 | 54.8 | 52.3 | 50.8 | 50.8 | 50.8 | 58.8 | 60.8 | | 60.1 | 55.1 | 51.1 | 60.1 | | 61.1 | 61.1 | 53.1 | 57.1 |
| POLOXAMER 407 | | | | | | | | | 60.1 | | | | | 60.1 | | | | |
| Emsorb 2726 | 12.5 | 7.5 | 12.5 | 9 | 5 | 3 | 3 | 0 | 3 | 3 | 3 | 3 | 3 | 3 | 4 | 3 | 3 | 3 |
| Stearyl Alcohol | 9.2 | 10.5 | 8 | 7 | 11 | 13 | 15 | 16 | 15 | 15 | 15 | 15 | 15 | 15 | 10 | 8 | 15 | 15 |
| Insoluble Saccharin | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 |
| Propyl gallate | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Spicemint Flavor | 4 | 4 | 4 | 4 | 4 | 4 | 4 | 4 | 5 | 5 | 5 | 5 | 5 | 5 | 5 | 5 | 5 | 5 |
| Vanilla Mint Flavor | 4 | 4 | 4 | 4 | 4 | 4 | 4 | 4 | 5 | 5 | 5 | 5 | 5 | 5 | 5 | 5 | 5 | 5 |
| tetrasodium-pyrophosphate | 8 | 14 | 14 | 10 | 10 | 10 | 10 | 10 | 10 | | 10 | 14 | 4 | | 6 | 6 | 10 | 6 |
| dicalcium phosphate | | | | | | | | | | 10 | | | 6 | 10 | | | | |
| Microcrystalline Wax ML 445 | | | 10 | 10 | 10 | 0 | 0 | 0 | 0 | 5 | 5 | | 0 | 7 | 10 | 7 | 7 |
| Triclosan | 3.3 | 3.3 | 3.3 | 3.3 | 3.3 | 3.3 | 3.3 | 3.3 | | | | | | | | | | |
| Observation | | | | | | | | | | | | | | | | | | |
| Need heat to wind | y | | n | y | Y | n | y | y | y | y | y | y | y | y | y | y | y | y |
| Bobbin tack(1 = poor, 5 = good) | 1 | | 5 | 5 | 3 | 4 | | 4 | 3 | 2 | 4 | 4 | 3 | 3 | 4 | 3 | 4 | 4 |
| Flake resistance | | | | | | | | | | | | | | | | | | |
| Feels sticky(1 = no, 5 = very) | | | | 5 | 4 | 4 | 2 | 1 | 2 | 2 | 3 | 3 | 3 | 1 | 4 | 3 | 4 | 4 |
| Load of two samples | 29/19 | na | na | 43/50 | 28/11 | 53/39 | 58/43 | 33/20 | 51/40 | 33 | 46/53 | 40/39 | 38/38 | 50/37 | 48 | 45 | 38/39 | 43/39 |

In a preferred embodiment of the invention, the improvements described and illustrated in FIGS. 1 through 4 are included on both lateral edges of the monofilament tape. However, modified edges can be included on only one edge of the tape if so desired.

Figure 5:
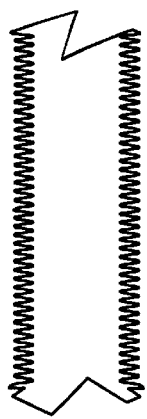
FIGS. 5–7 illustrate feather-edged tape where "fingers" are post-formed after extruding and drawing on one or both laternal edges of the monofilament tape.
Figure 6:
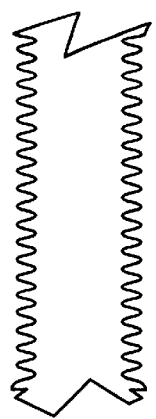
Figure 7:
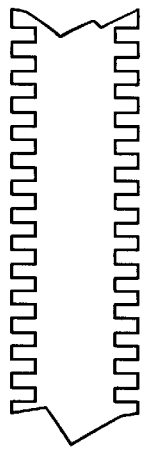
Figure 8:
FIGS. 8–13 illustrate various self-indicating monofilament tapes, each with visual indicators to assist the user of the tape.
Figure 9:
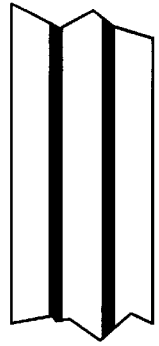
Figure 10:
Figure 11:
Figure 12:
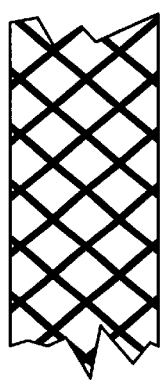
Figure 13:

A second physical improvement includes feather-edged tape where "fingers" are post-formed after extruding and drawing on one or both laternal edges of the monofilament tape such as illustrated in FIGS. 5 through 7. The space between "fingers", length of the fingers and shape of these fingers are determined by the type of mechanical edge cutting means employed to produce these "edge-fingers". Preferably, these "fingers" are produced on the monofilament tapes described in Tables 1 through 4 prior to coating the tape with various coatings described in Tables 1 through 5.

During flossing, these "fingers" create the user-perception that the floss is working, cleaning and removing plaque, biofilms, material alba, etc., while delivering saliva soluble coatings containing abrasives, cleaning substances and chemotherapeutic substances interproximally, at the gingival margin and subgingivally. The traditional "sawing motion" used to work the tape between teeth produces a "sweeping action" with the "fingers". This is generally perceived as improved gentleness.

This sweeping action is preferably accomplished by providing the monofilament dental tape edge with a series of closely spread slits latitudinally part way across the tape at or near 90° to the length of the tape. Varying the frequency and depth of these lateral slits allows for the production of a wide range of effects-in-use, both actual and perceived. The requisite break strength of the tape is maintained by the majority of the tape surface running, uncut, in the long direction of the tape. With the oriented polymers of the Fibaclean tapes described in Table 1, this break strength is essentially uncompromised by the edging process of the present invention. The lateral edge slits do not self-propagate, since the molecules of the polymers in most tapes are primarily aligned in the longitudinal direction of the drawing of the tape as it is extruded. Following such molecular orientation, such monofilament tapes with modified edges are difficult to tear in the cross-orientation direction.

The modified edges can be created either (1) off-line as a separate step, (2) in-line just before the take-up winder of the extrusion/drawing process or (3) in-line just before coating with coatings as described in Table 5. One could also position the slit cutting mechanism detailed in the accompanying figures after the tape is coated and just before the take-up winders.

Monofilament dental tapes are typically 0.05 to 0.1 inches wide and 0.002 to 0.004 inches thick, although tapes of larger or smaller dimensions would also be suitable for use in this invention. Since the chosen dimensions can be selected from such a wide range, the monofilament tape illustrations in the Figure are of unspecified dimensions and those persons having ordinary skill in this art will adjust the dimensions to produce the desired level of strength and effect.

A third physical improvement in coated monofilament tapes includes self-indicating monofilament tapes where the various flake-resistant "coatings" as described in Tables 1 through 5 can include a design and/or different colors for purposes of signaling to the user that the type of coating released and/or the release, per se, of the coating from the monofilament tape during flossing into the area flossed.

Examples of six various self-indicating monofilament tapes are illustrated in FIGS. 8–13. These visual-indicating tapes can combine various means for post "scribing" the coating to the designs illustrated in FIGS. 8–13, where the monofilament tape is either natural color or pigmented to produce a "color contrast" when the coating is scribed.

In the original construction of the monofilament tape substrate, at some point the polymeric substance (e.g. Teflon®, thermoplastic resin, etc., as described in Tables 1 through 4 is molten and processed with a typical screw extruder. See PCT Publication No. WO 98/50607 and U.S. Ser. No. 09/330,491 for an especially preferred monofilament tape substrate. The disclosures of these two patent applications are hereby incorporated herein by reference. Such tape is commercially available from the Perident Company under the brand name Fibaclean.™

Into the melt is introduced FDA approved colorants for plastics, most typically as a "color concentrate" where the colorant is compounded into the base resin or a resin compatible with the base resin. This "color concentrate" is then mixed with the base resin in the appropriate ratio (typically 1–5%) and as the melting-mixing-extrusion occurs the color is uniformly distributed throughout the resultant monofilament tape thereby coloring the tape with little or no effect on the physical parameters of the tape.

The colored monofilament tape is coated as described in copending Provisional Application Serial No. 60/227,196. The coating is modified to produce a desired level of opacity, ranging from slightly translucent to opaque. This is accomplished most easily with finely divided $TiO_2$ such as used to opacify toothpaste. Alternatively, higher levels of opaque oral care ingredients such as chalk, silica or dicalcium phosphate and/or ingestible pigments such as FD&C flakes may be used in the coating described in Tables 1 through 5.

The resultant monofilament tape, preferably coated to a thickness of from 0.001 to 0.004 inches on each side with the coating, will appear white if $TiO_2$ is used as the opacifier except at the edges of the tape. The degree of whiteness can be adjusted for appearance reasons from a pastel of the virgin tape color to almost pure white. The greater the contrast with the virgin tape, the more easily the user can discern the release of the coating from the tape and the corresponding delivery of the coating substances subgingivally and/or between the interproximal spaces as evidenced by the indicator color on those areas of the tape where the active ingredient has been depleted.

The visual stripe can be produced by selectively removing, with a flexible, non-abrading scribe, opaque versions of coatings as the tape line moves downstream to the take-up winders. If these flake-free coatings described in Tables 1 through 5 are not desired, then a thin coating of microcrystalline wax or so-called water-soluble waxes may be opacified with $TiO_2$ or other food grade opacifier, either white or colored and then applied first to the tape in the conventional manner or any other application technique suitable for applying such substances.

The flexible, non-abrading scribes or styles can be arranged to track the length of the tape to produce the lengthwise stripe or stripes. In many embodiments it is convenient to use the standard tape driving godets situated just before the take-up winders as the platform against which the scribes exert pressure to remove the overlaying opaque substance. Other platforms or rollers across which the tape is drawn can also be installed downstream from the opaque ingredient loading section. To produce barber-pole stripes, the scribes are moved across the monofilament tape at 90° to the tape as it travels downstream. The frequency of the stripe is determined by the interval of the scribes and the angle of the stripe can be adjusted by changing the ratio of the tape speed and the scribe speed.

Stripes which are color-on-white can be produced by a mixing into the chemotherapeutic coating or wax, a colored opacifier, such as an FD&C lake or natural opaque pigment, then coating over a white monofilament tape. Stripes which are white-on-color can be produced by a mixing into the chemotherapeutic coating or wax a white opacifier, such as the $TiO_2$ or other food grade opacifier described above, then coating over a colored tape.

The scribes can be prepared from flexible bristles, such as are used in brushes, selected form polymers with equal or lower hardness indices than the tape which is being striped. Wider stripes can be produced with flat, flexible scribes or a cluster of bristles as in a toothbrush. The physical placement of the scribes and their movement across the tape face will vary, depending on the visual stripe design desired. Several of these arrangements, sufficient to illustrate the principle are shown in the accompanying drawings, but the number of arrangement are almost limitless, once the principle herein disclosed is understood.

A suitable coated monofilament tape which can be physically improved according to the teachings of the present invention is described in Example 1 below:

EXAMPLE 1

A modified thermoplastic elastomer based dental tape, suitable for the present invention is produced as follows:

PEBA granules (PEBAX® 5533 pellets) are dried and fed into an extrusion hopper. In another hopper, a tumble blended masterbatch of Titanium Dioxide ($TiO_2$) (plus polypropylene (PP) carrier) and processing aid Dow Corning MB-50-001 ultra-high molecular weight silicone (PDMS) dispersed in polypropylene (PP).

The ratio of PEBA and Masterbatch are:
90% PEBA
10% Masterbatch (broken down to 20% $TiO_2$/PP and 80% PDMS/PP)
(The white Master is 60% $TiO_2$; 40% PP and the silicone is 50:50)

The temperatures used in production are as follows (with the processing range in brackets.)

In the extruder, the following processing conditions are followed:
Feed Zone: 220° C. (200°–230°)
Compression (Mid) Zone: 260° C. (240°–280°)
Metering Zone: 260° C. (240°–280°)
Filter Zone: 260° C. (240°–280°)
Pump Zone: 260° C. (240°–280°)
Die Zone 1: 270° C. (250°–285°)
Die Zone 2: 270° C. (250°–285°)
Die Zone 3: 270° C. (250°–285°)
Pressures at 3 points are controlled:
Pre-filter: 1200 psi (1000–1400)
Pre-pump: 1200 psi (1000–1400)
Die Head: 200 psi (100–300)
Metering Pump: 9.3 rpm (8–11)

The extruder produces 12 PEBA tapes from a die with holes cut to 8 mm×0.375 mm.

From the extruder, the tapes are introduced into a water bath for cooling: The water lies 5–10 mm vertically from the die, and is kept at 19–21° C. The 12 ends on the tape are then fed under a guide bar, then up at an angle of 45° to a water removal fan bar. A second water removal bar is vertically above this, allowing the extrudate to form an 'S' shape.

The pulling action required to take the extrudate through the water bath and water removal bars is achieved by a set of initial haul-off rollers. This is a set of 5 rollers (3 on top, two below), in which the final two rollers through which the ends pass are heated.
Roller haul-off setting: 15.3 meters per minute (14–16)
Heat Rollers (both): 100–110° C. (95°–120°)

After cooling, the tapes are drawn as follows:
The ends are drawn over a hot plate with a speed increase, controlled by a second set of 5 rollers.
Hot plate temperature: 130° C. (120°–140°)
Roller Speed: 103 meters per minute (95–110)
These rollers are not actively heated or cooled.

After drawing, there is a 'relaxation stage' where a little stretchability is allowed back into the material, in addition to "setting" the final characteristics. Once again, a 5-roller set-up as described above is used to pull the ends over a hot plate. This set of rollers are chilled by circulating water through a chiller.
Hot plate temperature: 130° C. (120°–140°)
Roller Speed: 100 meters per minute (92–107)
Circulating Water temperature: 18° C. (16°–20°)

The ends are then wound onto phenolic cones, which have independent tension and torque control, which is adjusted to conditions. The final product specifications for this run were:
Width: 1.3 mm+/−0.1 mm
Thickness: 0.060 mm+/−0.01 mm
Decitex: 650–800
Break Strength: >25 N
Elongation: 25–40%

The final product was then coated with a crystal-free, substantially flake-free, saliva soluble coating as described and claimed in co-pending Provisional Patent Application Serial No. 60/263,220, using the coating process as described and claimed in said co-pending patent application.

Finished coated versions of this tape were then consumer tested in a sequential, monadic, home placement test against uncoated tape and Glide®. The coated modified TPE tape of the present invention was preferred over the other tapes on each of 11 key attributes.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. Physical improvements in coated elastomeric monofliament dental tapes wherein said coating comprises a crystal control substance, is substantive, substantially flake-free, saliva soluble, and is substantially crystal free,
said physical improvement being selected from the group consisting of:
    (a) a reduced cutting edge wherein during monofilament tape extrusion, at least one lateral edge of said tape is formed into various shapes selected from the group consisting of: rounded shapes, multiple rounded shapes, thin flexible edges, multiple thin flexible edges and combinations thereof,
    (b) feathered lateral tape edges comprising multiple fingers of varying densities and varying lengths introduced by various continuous cutting means applied to at least one edge of said tape after extrusion and prior to coating,
    (c) self-indicating features incorporated into said coatings using a combination of colored tapes and colored tape coatings wherein various scribes applied to the coatings remove portions of the coating to form a visual predetermined design, and (d) combinations thereof.

2. An improved elastomeric monofilament dental tape according to claim 1, wherein said reduced cutting edge is selected from the group consisting of bulbous edges, multiple feathered edges barbell shapes, and foldable thin edges.

3. An improved elastomeric monofilament dental tape according to claim 1, wherein said feathered lateral edge is selected from the group consisting of feathered edges with a plurality of fingers on one or both of the lateral edges.

4. An improved elastomeric monofilament dental tape according to claim 1 wherein said self-indicating feature is selected from the group consisting of a single colored linear stripe, multiple colored linear stripes, multiple angled stripes, and cross-hatch stripes.

5. A process for physically improving coated elastomeric monofilament dental tapes wherein said coating comprises a crystal control substance, is substantive, substantially flake-free, saliva soluble, and is substantially crystal free, said process comprising at least one of the following steps:

(a) reducing the monofliament tape cutting edge effect, wherein during tape extrusion, at least one lateral edge of said tape is formed into various shapes selected from the group consisting of rounded shapes, multiple rounded shapes, thin flexible edges, multiple thin flexible edges and combinations thereof, (b) forming feathered lateral tape edges after tape extrusion by applying continuous cutting means to at least one edge to produce lateral edge tape fingers at various densities and various lengths, and (c) incorporating into colored monofilament tapes having colored coatings, various designs by removing a predetermined amount of said coating using scribe means to create a visual predetermined design in said coating.

6. A method for improved cleaning of interproximal, subgingival and gingival margin areas of the oral cavity comprising flossing these areas with a coated elastomeric monofilament dental tape wherein said coating comprises a crystal control substance, is substantive, substantially flake-free, saliva soluble, and is substantially crystal free, and wherein said tape has one or more feathered lateral tape edges comprising multiple fingers of varying densities and varying lengths.

7. A method for improved cleaning of interproximal, subgingival and gingival margin areas of the oral cavity comprising flossing these areas with a coated elastomeric monofilament dental tape wherein said coating comprises a crystal control substance, is substantive, substantially flake-free, saliva soluble, and is substantially crystal free, and said tape has at least one edge of said tape selected from the group consisting of rounded shapes, multiple rounded shapes, thin flexible edges, multiple thin flexible edges and combinations thereof.

* * * * *